US00PP09740P

United States Patent [19]

Dümmen

[11] Patent Number: Plant 9,740

[45] Date of Patent: Dec. 10, 1996

[54] POINSETTIA PLANT NAMED HWD MENORCA

[75] Inventor: Günter Dümmen, Rheinberg-Eversael, Germany

[73] Assignee: Dummen Jungpflanzenkulturen, Rheinberg-Eversael, Germany

[21] Appl. No.: 516,476

[22] Filed: Aug. 17, 1995

[51] Int. Cl.[6] ..... A01H 5/00

[52] U.S. Cl. ..... Plt./86.4

[58] Field of Search ..... Plt./86.4

*Primary Examiner*—James R. Feyrer

*Attorney, Agent, or Firm*—Proprietary Rights International

[57] ABSTRACT

A new and distinct cultivar of Poinsettia plant named HWD Menorca, characterized by its bright red flower bracts; large flower bracts; large showy cyathia, large number of flower bracts per inflorescence; medium to high vigor; large leaves; freely branching plant habit; and excellent postproduction longevity.

1 Drawing Sheet

The present invention relates to a new and distinct cultivar of Poinsettia plant, botanically known as *Euphorbia pulcherrima* Willd., known as the variety Duemenorca, and hereinafter referred to by the cultivar name HWD Menorca.

The new cultivar is a product of a planned breeding program conducted by the inventor in Rheinberg, Germany. The objective of the breeding program was to develop a new bright red variety with excellent postproduction longevity.

The new cultivar originated from a cross made by the inventor of the cultivar V-10 (U.S. Plant Pat. No. 4,235) as the male or pollen parent with the nonpatented cultivar Steffi as the female or seed parent.

The cultivar HWD Menorca was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Poinsettia are stabilized and reproduced true to type in successive generations of asexual reproduction.

The following traits have been repeatedly observed and are determined to be the unique characteristics of HWD Menorca. These characteristics in combination distinguish HWD Menorca as a new and distinct cultivar:

1. Bright red flower bracts.
2. Large flower bracts.
3. Large number of flower bracts per inflorescence.
4. Large, showy cyathia.
5. Medium to high vigor.
6. Large leaves.
7. Freely branching plant habit.
8. Excellent postproduction longevity.

In comparison to the parent cultivar V-10, the new Poinsettia has brighter red flower bracts; large flower bracts; is more vigorous; larger leaves; longer postproduction longevity as foliage and cyathia are retained longer on the new Poinsettia compared to V-10; and flowers 3 to 7 days later. In comparison to the parent cultivar Steffi, the new Poinsettia is more vigorous and has larger leaves and flower bracts.

The accompanying colored photograph illustrates the overall appearance of the new cultivar, showing the colors as true as it is reasonably possible to obtain in colored reproductions of this type. The photograph comprises a top perspective view of a typical potted plant of HWD Menorca with on pinched plant in a 15-cm container.

The cultivar HWD Menorca has not been observed under all possible environmental conditions. The phenotype may vary somewhat with variations in environment such as temperature, daylength and light intensity, without, however, any variance in genotype, The following observations, measurements and comparisons describe plants grown in Rheinberg, Germany, under commercial practice in a glass-covered greenhouse with day temperatures of 22° C. and night temperatures of 18° C. and light levels of 30,000 to 40,000 lux.

In the following description, color references are made to the Royal Horticultural Society Colour Chart except where general terms of ordinary dictionary significance are used.

Classification:

*Botanical.*—*Euphorbia pulcherrima* Willd.

*Commercial.*—Poinsettia.

*Cultivar.*—'HWD Menorca'.

Parentage:

*Male parent:* 'V-10' (U.S. Plant Pat. No. 4,235).

*Female parent:* 'Steffi'.

Propagation:

*Type cutting.*—Terminal cutings.

*Time to initiate roots.*—Summer: 27° C., 21 days. Winter: 20° C., 28 days.

*Rooting habit.*—Fine, freely branching.

Plant description:

*Plant form.*—Vase-shaped.

*Growth habit.*—Freely branching and upright. Branching is enhanced by the removal of the apical shoot tip. Medium to high vigor.

*Foliage description.*—Arrangement: Opposite. Size: Length: 13 cm. Width: 9.5 cm. Shape: Deltoid. Tip: Acuminate. Base: Acute. Margin: Entire and sometimes lobed. Texture: Upper side: Velvety, glabrous. under side: Pubescent at veins, very fine pubescence. Color: Young foliage upper side: 147A. Young foliage under side: 147B. Mature foliage top side: 147A. Mature foliage under side: 147B. Venation: Upper side: 146D. Under side: 146D. Petiole: Pattern: Pinnate. Length: 7 cm. Color: 146D.

Flower description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under short day/long night conditions.

*Time to flower.*—8.5 to 9 weeks under short day/long night conditions.

*Quantity of inflorescences.*—10 to 15 cyathia per corymb.

*Inflorescence size.*—Diameter: 29 cm. Height (depth): 7 cm.

*Flower bracts.*—Attitude: Horizontal to stem axis. Quantity of flower bracts: 19 per inflorescence. Size: Length: 10 to 13.5 cm. Width: 6 to 7.5 cm. Shape: Elliptic. Tip: Acuminate. Base: Acuta. Margin: Usually entire, sometimes lobed. Texture: Upper side: Satiny, glabrous. Under side: Smooth, glabrous. Color: When opening: In between 46B and 46C. Mature, top side: In between 46B and 46C Mature, under side: 46D. Fading to: Flower bract color does not fade. Venation: Upper side: 46C. Under side: 46D. Petiole color: 146D.

*Cyathia.*—Quantity: 10 to 15 per corymb. Color: Immature: 144A. Mature: 144C. Size: Length: 1 cm. Width: 0.5 cm. Diameter of cyathia cluster: 4 cm. Stamens: Stamen number: 40 to 50 per cyathium. Anther size: 1 mm. Anther color: 187B. Pollen color: 10C. Pistils: Pistil number: 1 per cyathium. Stigma color: 187B. Style color: 187B. Style length: 3 mm. Ovary number: 3. Nectaries: Usually one or two per cyathium.

Disease resistance: No fungal, bacterial nor viral problems observed.

Postproduction longevity: Generally more than 5 weeks under interior conditions.

It is claimed:

1. A new and distinct cultivar of Poinsettia plant named HWD Menorca, as illustrated and described.

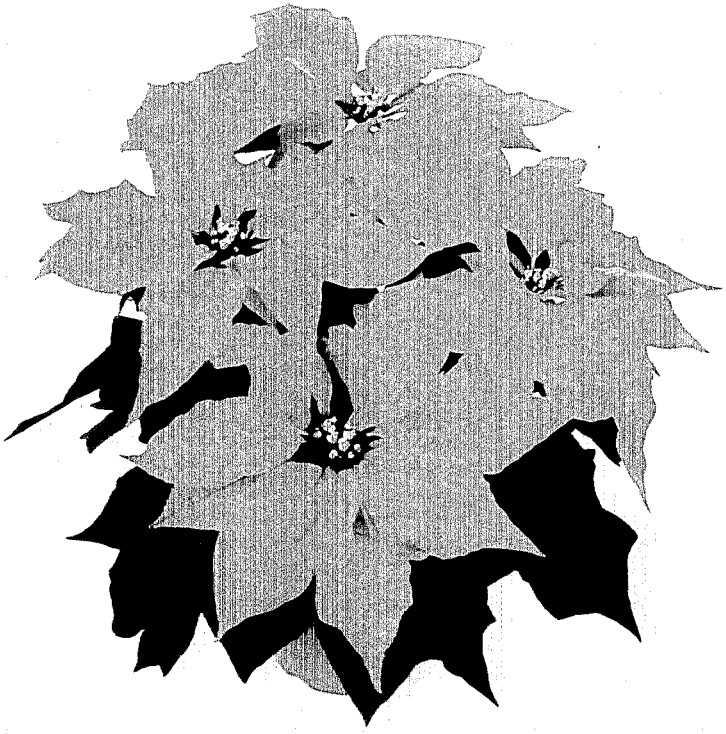

* * * * *